United States Patent

Clark et al.

Patent Number: 5,258,612
Date of Patent: Nov. 2, 1993

[54] TIMED-RESOLVED SPECTROSCOPY WITH SPLIT PUMP AND PROBE PULSES

[76] Inventors: William G. Clark, 24 Chatham Woods, Pittsford, N.Y. 14534; Philippe Bado, 3633 Huron Ct., Ann Arbor, Mich. 48103; Edward F. Gabl, 431 Glenbrook Ct., Saline, Mich. 48176

[21] Appl. No.: 861,916

[22] Filed: Apr. 1, 1992

[51] Int. Cl.$^5$ .................................. G01J 3/50
[52] U.S. Cl. ...................... 250/226; 356/432
[58] Field of Search ............ 250/216, 214 R, 226; 356/432, 308, 309

[56] References Cited

U.S. PATENT DOCUMENTS

| | | | |
|---|---|---|---|
| 4,636,088 | 1/1987 | Rosencwaig et al. | 374/5 |
| 4,854,710 | 8/1989 | Opsal et al. | 356/432 |
| 4,952,063 | 8/1990 | Opsal et al. | 356/432 |
| 5,042,952 | 8/1991 | Opsal et al. | 356/432 |
| 5,062,715 | 11/1991 | Nakata et al. | 356/432 |

OTHER PUBLICATIONS

Hirschfeld, "Unconventional Spectroscopy"; Proc. Soc. of Photo-Optical Instrumentation Engineers; v. 82, 1976; pp. 53-65, 80-83.

Kushida et al, "Picosecond Fluorescence Spectroscopy . . . "; Semiconductors Probed by Ultrafaster Laser Spectroscopy, v. II, 1989; Academic Press.

Elzinga et al, "Pump/Probe Method for Fast Analysis . . . "; Applied Optics, v. 26, No. 19; 1 Oct. 1987, pp. 4303-4309.

Elzinga et al, "Pump/Probe Spectroscopy by Asynchronous Optical Sampling"; Applied Spectroscopy, v. 41, No. 1, 1987, pp. 2-4.

Salin et al, "Single-Shot Measurements of a 52-fs Pulse"; Applied Optics, v. 26, No. 21, 1 Nov. 1987, pp. 4528-4531.

Rodwell et al, "Subpicosecond Laser Timing Stabilization"; IEEE Jour. Quantum Electronics; v 25, No. 4, Apr. 1989; pp. 817-827.

Darack et al, "Timing-Jitter Stabilization of a Colliding-Pulse Mode-Locked Laser . . . "; Optics Letters, v. 16, No. 21, 1 Nov. 1991; pp. 1677-1679.

Spence et al "Regeneratively Initiated Self-Mode-Locked Ti: Sapphire Laser"; Optics Letters, v. 6, No. 22, Nov. 15, 1991; pp. 1762-1764.

Chen et al, "1.9 Picosecond Optical Temporal Analyzer . . . "; International Electron Devices Meeting; Technical Digest, Dec., 1991; pp. IEDM 91-417-20.

Primary Examiner—David C. Nelms
Attorney, Agent, or Firm—Cumpston & Shaw

[57] ABSTRACT

In a pump/probe experiment, information about an event is detected and correlated with an accumulatable quantity representing the elapsed time interval between the arrival of the pump and probe pulses at the experiment. The accumulatable quantity is used to configure the pump and probe sources to eliminate temporal resolution problems caused by pulse timing jitter, the complexity of amplification, continuum generation, and subsequent reamplification, as well as data acquisition rate limitations. Two pulse sources serve as pump and probe pulses respectively. Each pulse is directed at the experiment. A portion of each pump pulse is diverted to a detector before it reaches the experiment, and a portion of each probe pulse is diverted to another detector. The pump and probe pulses are no-coincident in time at the experiment. Quantities related to the time difference and the information imposed on the probe pulse by the experiment are accumulated to obtain data about the temporal evolution of the event.

37 Claims, 2 Drawing Sheets

TIMED-RESOLVED SPECTROSCOPY WITH SPLIT PUMP AND PROBE PULSES

TECHNICAL FIELD

This invention relates to pump/probe experiments wherein pump pulses initiate events in experiments, while probe pulses probe the experiments from time to time in order to extract therefrom information about the experiment for observing the time-dependent behavior of said events. In particular, the present invention relates to method and apparatus for use in such experiments.

In this form of what we call time-resolved spectroscopy, it is of interest to observe time-dependent behavior of an event at very small time intervals and to do so with pump and probe pulses from independent sources so that the oscillating wavelength of each can be altered to fit the needs of the experiment. It is also desirable to accumulate data at rates that are higher than the present use of mechanical optical delay lines will allow, in experiments in which the pump and probe pulses originate from the same source. Moreover, for studying events that occur in extremely short time intervals of less than about 10 picoseconds, the use of independent pump and probe sources in time-resolved spectroscopy is difficult because pulse timing jitter degrades temporal resolution. And while pulse timing jitter is eliminated in pump/probe experiments when both pulses originate from the same oscillator, such systems are limited in the rate at which they can scan the time interval of interest because of their use of mechanical optical delay lines. An additional limitation of this technique is that it is difficult to obtain pump and probe pulses at a wide variety of wavelengths without resorting to the expensive process of amplification and continuum generation, and even then it is often necessary to re-amplify the desired portion of the continuum to obtain sufficient energy to initiate, or pump, an experiment.

Presently, the problem of prior art is to provide method and apparatus which allow observation of events that occur on picosecond and subpicosecond time scales with sources that have the flexibility to be used at differing wavelengths and energies, and can acquire data at reasonably high data acquisition rates.

BACKGROUND ART

Insofar as we are aware, the so-called ASOPS approach represents the best present state of the art of such apparatus and method.

Elzinga et al, for example, in an article entitled "Pump/Probe Method for Fast Analysis of Visible Signatures Utilizing Asynchronous Optical Sampling" (ASOPS), in Applied Optics, Vol 26, No. 19, pp 4303-4309, Oct. 1, 1987, describe monitoring subnanosecond excited-state processes by stimulating a process with pump pulses from a mode-locked laser and probing it with probe pulses from an asynchronously pumped laser. The two lasers operate at slightly different repetition rates, so a repetitive relative phase walk-out of pump and probe pulses occur.

In other prior pump/probe methods, the pump and probe pulses run at identical repetition rates, with an optical delay line used to control relative timing between the pulses.

DISCLOSURE OF THE INVENTION

According to the present invention, information about the event is extracted from the experiment by standard detection means, and correlated with an accumulatable quantity that represents the elapsed time interval between the arrival of the pump and probe pulses at the experiment. By means of this accumulatable quantity we can now configure our pump and probe source(s) in a multitude of ways so as to eliminate temporal resolution problems caused by pulse timing jitter in the ASOPS approach, or the complexity of amplification, continuum generation and subsequent re-amplification as well as data acquisition rate limitations imposed by mechanical optical delay lines in the "single oscillator source" approach.

One form of the preferred embodiment we refer to as time interval measurement, or TIMe, pump/probe spectroscopy. Here two pulse sources serve as sources of pump pulses and probe pulses, respectively, in time-resolved experiments. Each pulse is directed at the experiment. Conveniently, before any pump and probe pulse reaches the experiment, a portion of each pump pulse is diverted to a detector, and a portion of each probe pulse is diverted to another detector.

The operating parameters of the sources may be chosen to be such that, in general, pump pulses will be non-coincident in time with the probe pulses at the experiment.

The portions of the probe and pump pulses directed at the experiment have interacted with material or device therein. The pump pulse initiates an event in the material or device therein. For example, the event can be a chemical reaction from which a transient species evolves in response to the pump pulse, in which case the probe pulse would interact with such species such as to be affected thereby.

In other words, after interacting with the event, the probe pulse has had imposed thereon an information signal relating to the temporal evolution of the event.

Suitable hardware, including the detectors, provides a quantity which is a measure of the aforesaid time interval, and also a second quantity which is a measure of the information signal imposed on the probe beam at the end of that time interval.

These two quantities are accumulated, as a pair of corresponding associated numbers, by a suitable data acquisition system. The pump/probe process is repeated many times over in order to obtain sets of event information signals and time intervals which may be averaged, and/or otherwise manipulated in order to obtain data about the temporal evolution of an event over the experimental time regime of interest to the experimenter.

In the preferred embodiment of the present invention, the TIMe technique can also provide the time delay of prior art pump/probe systems by employing the concept of the accumulatable quantity, thereby obviating the prior art's need to maintain precise synchrony (or asynchrony) between pump and probe sources, or to reduce pulse timing jitter below the desired temporal resolution of the experiment, or to provide a scanning optical delay between the beams. It is to be noted, however, that the TIMe technique can be used to provide synchrony (or asynchrony) of pump and probe sources, that is, it is not dependent on the manner in which time delay between beams is provided.

In addition, higher pulse energy and a large range of wavelengths are available from the broad range of mode-locked laser oscillators now employable.

DETAILED DESCRIPTION OF PREFERRED EMBODIMENTS

Figure 1:
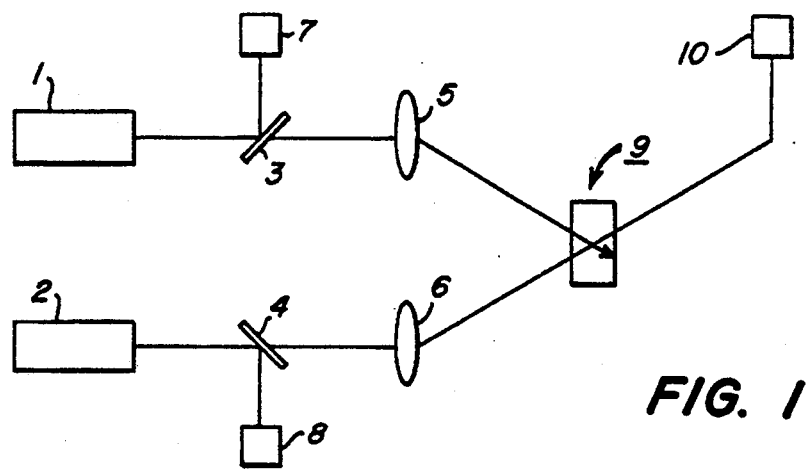
FIG. 1 is a diagram of a TIMe apparatus according to the invention.

A preferred form of apparatus according to the invention, as shown in FIG. 1, comprises sources 1 and 2, beam splitters 3 and 4, optics 5 and 6, pulse detectors 7 and 8, experiment 9, and signal detector 10. Sources 1 and 2 respectively provide pump pulses and probe pulses.

Beam splitter 3 and optics 5 function as pulse directing means for directing each pump pulse to the pulse detector 7 and to the experiment 9. Likewise, beam splitter 4 and optics 6 function as pulse directing means for directing each probe pulse to pulse detector 8, and to the experiment 9.

The time intervals result from arranging the system elements such that the trains of pulses emerging from the sources are on the whole non-coincident. While such arrangement can be achieved in a number of ways, in the present example of the invention, this is achieved by providing the sources 1 and 2 which function independently of one another. For example, each could be designed to have the same nominal pulse repetition rate as the other, yet while there would be instances of pulse coincidence, there would also be instances of non-coincidence of pulses. We prefer, however, that the pulses from pump laser 1 be 10 nanoseconds apart, and that the pulses from the probe laser 2, be 10.01 nanoseconds apart. Assuming that the lasers are ideal oscillators, then pulse coincidence can occur every 10 microseconds, so most of the time there will be non-coincidence.

Figure 2:
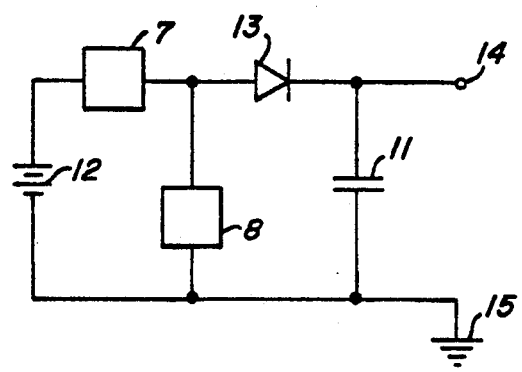
FIG. 2 shows a quantity accumulation and pulse detection scheme which may form part of the apparatus of FIG. 1.

According to the invention, the event information is provided to a suitable data acquisition system (DAS) by transforming event information to accumulatable quantities, as, for example, FIG. 2 illustrates.

In FIG. 2, detectors 7 and 8 are photoconductors which, when they receive pulses from optics 5 and 6, respectively, become highly conductive, but are at other times, non-conductive.

Thus, when the detector 7 receives a pump pulse, charge from power supply 12 (here shown as a battery for simplicity) flows through a diode 13 to capacitor 11. Accordingly, the capacitor 11 accumulates a quantity of electrical charge in proportion to the time interval between that pump pulse and such time as the photoconductor becomes non-conductive again.

If, next, the detector 8 receives a probe pulse, it becomes conductive and grounds power supply 12, as indicated at 15. The diode 13, however, prevents the off-ground side of the capacitor from being grounded through the photoconductive detector 8.

When the system is operating, in general each pump pulse will be followed by just one probe pulse. Consequently, capacitor 11 charges when a pump pulse is detected, and then discharges when the probe pulse immediately following the pump pulse is detected. The net charge on the capacitor 11 will therefore represent the time interval by which a probe pulse follows the next-preceding pump pulse.

The power supply 12 is merely illustrative of charge sources. Any DC power supply would do. Conveniently, the DAS (not shown) could both provide the charging voltage, and discharge the capacitor 11 only at such times as it is desired to have pump/probe pulses produce charge on the capacitor, and to have the DAS accept information from the experiment.

It is also unnecessary to attempt to probe, i.e., sample every event-initiation. It will be understood that the charge on the capacitor must be measured, and that it must be discharged to ground potential before it is next charged, hence, between each measured pump pulse to probe pulse time interval, there can be another time interval (of which the length can be predetermined by one of ordinary skill in the art,) during which one or more pump/probe pulse pairs occur without being measured.

Figure 3:
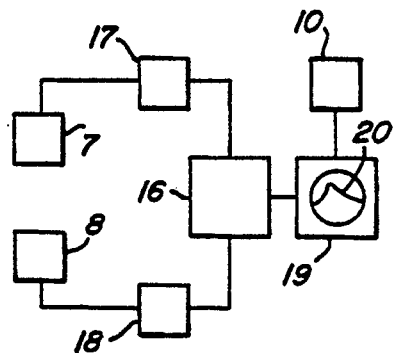
FIG. 3 shows apparatus which may be used with the quantity accumulation scheme of FIG. 2, for providing inputs to a data acquisition system.

In FIG. 3, the pulse detectors 7 and 8 are connected to a time to amplitude converter 16 (TAC), via constant fraction discriminators (CFD's) 17 and 18. The output of the TAC 16 is a voltage representative of the time interval between a pump pulse and a probe pulse, as more particularly described hereinbelow.

The TAC output voltage is connected to any suitable data acquisition system (DAS), for example, a digital oscilloscope 19 whose x-input receives that voltage, and whose y-input receives the output voltage of signal detector 10. In response, the oscilloscope produces an x vs y trace 10 of successive pairs of voltage, respectively representing pulse time intervals, and event information gathered during those time intervals. Trace 20 shows the temporal evolution of the experimental event/events.

The embodiment of FIG. 2 uses passive circuit components, which do not introduce "jitter" into the pulse information it is processing, e.g., photoconductive switches. However, reflections will be created by the transmission lines and interconnections associated with the devices, and will appear as jitter. Again, active devices may introduce too much jitter if one tried to use them to handle the very low amount of charge that would be delivered by them in one picosecond—so low that signal would be buried in ambient electrical noise. Thus, these teachings will be most useful for pump/probe experiments where the event time regime is long compared to the jitter introduced by the system hardware, etc.

For shorter time regimes, we increase the amount of delivered charge, whereby to improve the signal to noise ratio. In addition, we increase the time scale, i.e., multiply picoseconds time intervals to nanosecond levels, thereby allowing us to use good active components without having to worry about their jitter.

Figure 4:
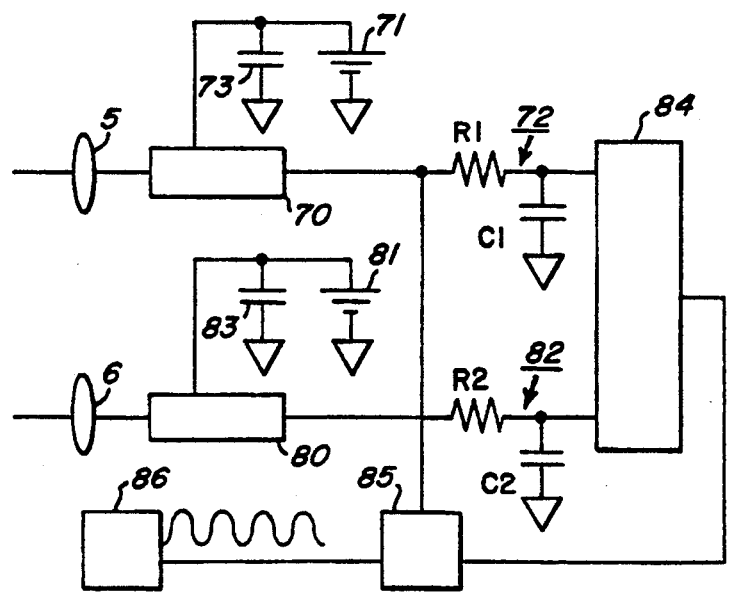
FIG. 4 shows a second form of quantity accumulation scheme for TIMe apparatus.

Thus, in FIG. 4, we provide photodetectors or photoconductor switches 70 and 80. These replace photoconductors 7 and 8, respectively, of FIG. 2, and feed the voltages of power supplies 71 and 81 to a pair of charging circuits 72 and 82 composed respectively of R1, C1 and R2, C2. The resistances and capacitances are chosen to be such that the quantity R1C1/(R1C1-R2C2) is equal to about 1000, whereby to establish a nanosecond regime. If necessary, capacitors 73 and 83 can be provided in order to assure that sufficient charge will be available for charging $C_1$ and $C_2$.

When it is zero, the charge differential between the capacitors causes a comparator 84 to produce an output voltage. At the same time that $C_1$ is being charged through switch 70, a fast counter 85 also receives charge from switch 70, and is caused thereby to count pulses or cycles from a fast oscillator or clock 86 operating at, say, 100 MHz. When the capacitors $C_1$ and $C_2$ have the same voltage, the comparator 84 produces an output voltage which stops counter 85. Thus, the number of counts divided by 1000 is a measure of the time between pump and probe pulses.

The active devices in the comparator 84, the switches 70 and 80, and the passive components of charging circuits 72 and 82 are stable, although the active devices could drift with temperature, in which case, they would be temperature compensated so as to prevent such drift, as by conventional means well known in the art.

While characteristically the spectrum of the pump pulse will be such as to be largely absorbed by the experiment, the spectrum of the probe pulse will be such as to be at least partially transmitted through the experiment, so as to be available for detection by signal detector 10.

Figure 5:
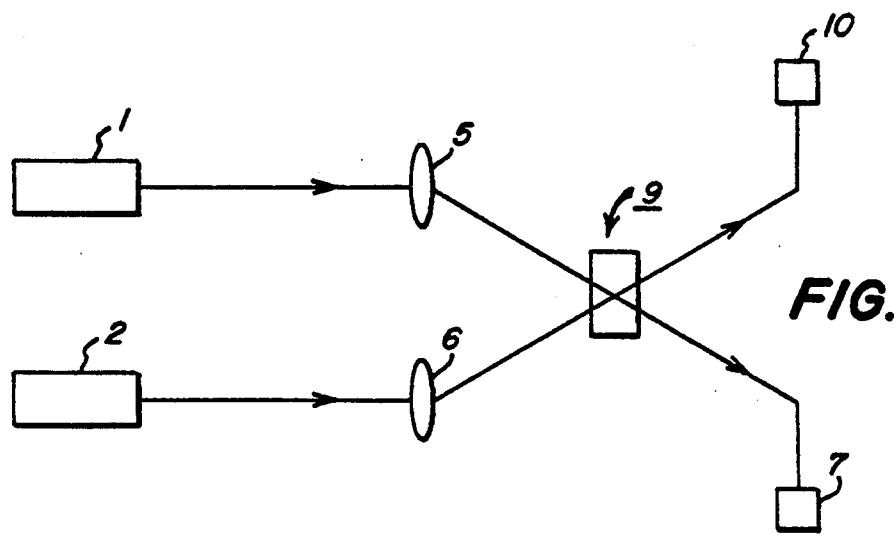
FIG. 5 shows a unitary form of pulse detection scheme.

As has been explained more fully hereinabove, the pulse detectors 7 and 8 provide for measuring time intervals, namely, the time elapsed between pairs of consecutive pump and probe pulses. Therefore, in principle, as shown in FIG. 5 should the experiment not absorb all of the pump and probe pulse, the pulse detector 7 could be located on the side of the experiment opposite to what FIG. 1 shows as the site of pulse detector 7. The signal detector 10 would then double as pulse detector 8, and the beam splitters 3 and 4 would be omitted. For those skilled in the art, other geometries are possible: e.g. all reflective schemes, etc.,as would be useful in picking up scattered light from the event. However, it is easy enough to dimension the apparatus shown in FIG. 1 so that there would be no significant discrepancies in arrival times due to splitting pulses into multiple paths.

Regardless of the detection arrangement, pulse detection provides for creating the quantities needed for observing event behavior at the aforesaid time intervals.

In ASOPS as described by Elzinga, et al, the temporal resolution of the system employed was limited by two factors, pulse width and, more significantly, pulse timing jitter or phase noise between the two pulse sources. Because pulse timing jitter was initially much larger than the pulse width from each source, the temporal resolution of their system was poor. With modification, they were successful in reducing phase noise to about the pulse width of each source—which was about 1 ps.

Similar problems exist with most short pulse sources. While they may be able to produce pulse widths of several tens of femtoseconds, their pulse timing jitter can be 1000 times worse, or several tens of picoseconds—making them poor candidates for experiments that require femtosecond resolution. And while phase noise can be minimized by referencing their resonator cavities to an external oscillator, residual phase noise may still be on the order of 1 ps.

Figure 6:
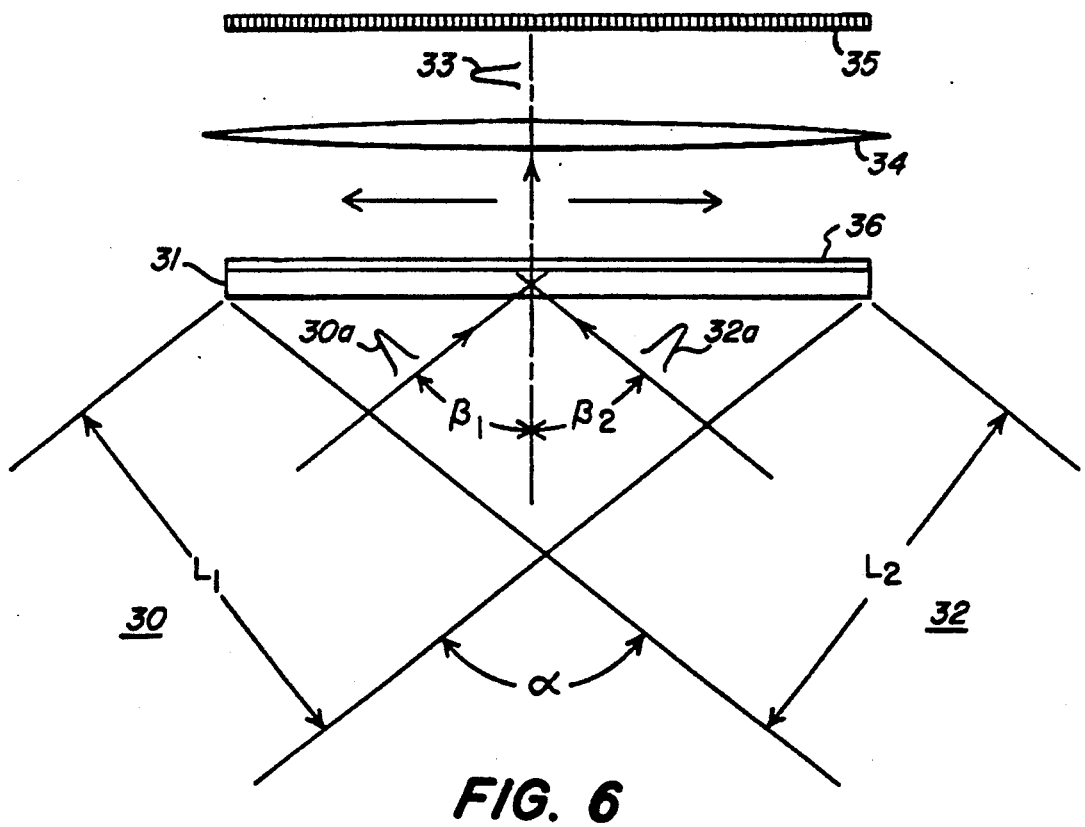
FIG. 6 shows a variation of a TIMe apparatus according to FIG. 1.

FIG. 6 shows a unitary form of TIMe pulse detection scheme that will address this problem. This geometry can also be a means for generating a signal by which the pulse timing jitter between two sources can be minimized, or for programming-in suitable delays between pump and probe pulses.

We expand pump pulse 30 beam diameter as shown by the dimension L1 and direct the expanded beam onto the sheet of material 31, at the angle B1. This can be done using a suitably designed cylindrical lens beam expander. Similarly, the probe beam 32 is expanded to the dimension L2 and directed onto the material 31 at the angle B2 which may be but is not necessarily the same as the angle B1 of pump beam 30. Both angles are measured from the normal to the material 31. Material 31 is a straight strip of uniform thickness, of a so-called "non-linear" material, e.g. 13130, KDP, etc.

A detectable quantity is produced when the two pulses 30 and 32 overlap in the material 31. For example, the material could be a crystal such that the overlap of pump pulse 30 and probe pulse 32 produces a third pulse 33 at a wavelength that represents the sum or difference frequency of pump pulse 30 and probe pulse 32. Or it could be an organic molecule with a two-photon absorption at the wavelength sum frequency of 30 and 32.

In any case it can be seen that pump pulse 30 sweeps across the material 31 from left to right. Similarly, probe pulse 32 sweeps across material 31 from right to left. Thus it can be observed that when the path lengths between the source of the pump pulse and the source of the probe pulse are identical and the two sources emit pulses in precise synchrony, then they will overlap in the center of the material 31. At the position of overlap, the material 31 will generate another pulse 33 that is imaged by the optical system represented by 34 onto an array detector 35.

A change in the arrival time between the pump and probe pulsed will cause a corresponding shift in the point where pump pulse 30 and probe pulse 32 overlap in the material 31. The result will be a measurable change in the position where the pulse 33 is generated in the material 31 and detected at the array 35. This change in position of 33 is a measure of the time delay between the pump and probe pulse. Optionally, a wavelength cut-off filter 36 may be provided for preventing pulses 30 and 32 from reaching the array 35.

Of course, this is a limitation imposed on the range of time intervals between the arrival of the pump and probe pulse at material 31, and thus their corresponding difference in arrival times at the experiment. This restriction is a practical one associated with size. But for reasonable size and cost arrays, the range of intervals could be several hundreds of picoseconds with sub-100 femtoseconds resolution, which is more than adequate for most ultrashort experiments. Data can be acquired and processed at kHz rates with relatively inexpensive, commercially available data acquisition boards.

While some synchrony between the pump and probe sources may be needed to keep them within the range of time intervals detectible by our TIMe scheme, this can be done using active cavity length stabilization as known to the prior art, (e.g., as in Spence et al, Darack et al, and Rodwell, et al)*. *OPTICS LETTERS/V. 16, No. 22/Nov. 15, 1991/pp. 1762-4; OPTICS LETTERS/V. 16, No. 21/Nov. 1, 1991/pp. 1677-9; IEEE J. QUANTUM ELECTRONICS/V. 25, No. 4/April, 1989/pp. 817-27, respectively. The virtue of our approach is that the pulse timing jitter is an advantage, as it provides for some random sample of time intervals that can be used to map out the temporal evolution of the event being investigated, whereas prior art pulse timing jitter was a disadvantage because it reduced temporal resolution. Indeed, it may be desirable to use the position signal from array detector 35 to program-in various time intervals so as to obtain a representative sample over the interval range of interest, and thus "induce" phase noise into the system. Or, it may be desirable to use this position signal to minimize pulse timing jitter between two oscillators still further, and thus produce more perfect synchrony between two sources.

Only ordinary skill in the art would be required to choose suitable components for use in the present invention. Suitable choices are presently available as follows:

Laser 1: Model CPM-1 Colliding Pulse Mode-locked Dye laser operating at 630 nm

Laser 2: Model NJA-2 Self mode-locked Ti:Sapphire laser operating at 780 nm.

Signal Detector 10: photomultiplier, Burle 1P28.

CFD's 17, 18: Ortec 935

TAC 16: Ortec 567

DAS 19: Multi-channel Analyzer.

Pulse detectors 7 and 8: Williamson-type Interdigitated photoconductors. N.B. In particular, the 1.2 picosecond photodetector disclosed by Y. Chen et al, in an article entitled "1.9 PICOSECOND OPTICAL TEMPORAL ANALYZER USING 1.2 PICOSECOND PHOTODETECTOR AND GATE, in International Electron Device Meeting, Washington, D.C. Dec. 8, 1991, page 417 PhB 3131192, possibly constructed on different substrates, like silicon or GaAs, which have different carrier lifetimes.

It is to be noted that all the foregoing specifications of components and circuit elements are exemplary, and will be sufficient guidance for those of ordinary skill in the art to choose equivalents, or make desirable modifications.

Suitable uses for the present invention include, electro optic and optical wave form sampling; experiments involving studying carrier dynamics and electromagnetic transient measurements in semi-conductors; experiments involving studying chemical reaction dynamics; and in general, making time-resolved studies of various kinds in chemistry, biology, physics, electronics, and other scientific/technological fields.

It is also to be noted that the use to which our invention is put will have a bearing on the nature of the pump and/or probe pulses. For instance, the foregoing description of our invention relates in great part to optical pulses. However, experiments can involve studying the properties of fast electronic devices and components, in which case the probe and pump pulses could be microwaves, as provided by microwave oscillators, e.g. masers, or photo-enhanced electron beams. We believe that the principles of our invention apply to microwaves, electron beams and electomagnetic radiation pulses in general, as well as to the above-described optical pulses.

In the foregoing we have described the preferred embodiments of our invention, and, as well, components, which we regard as suitable for use in our invention, and which are available commercially, or otherwise, e.g., constructible by technicians using only ordinary skill in the art of optics, electronics, and other skills of the maker of scientific and technical apparatus. Such description is intended solely as fulfillment of the requirements of Title 35, USC 112, first paragraph, and it is not to be taken as limiting the claims appended hereto.

Again, while we have also recited certain uses which may be made of our invention, these are merely exemplary. Such recital is not to be taken as limiting, for we believe that there likely are, or will arise, other suitable uses therefore, which we have not recited herein, but which those of ordinary skill in the art now recognize, or will in the future.

What is claimed is:

1. A method of performing pump/probe experiments, said method being of the type wherein a pump pulse and a probe pulse are directed at an experiment for initiating an event, and for probing said event for the purpose of observing the time-dependent behavior of said event, respectively, said method having the improvement comprising the steps of:
    a) splitting the pump pulse into a first pulse and a second pulse, said first pulse being directed at said experiment for initiating said event therein;
    b) splitting said probe pulse into a third pulse and a fourth pulse, said third pulse being directed at said event for probing said event;
    c) starting the accumulation of an accumulatable quantity in response to said second pulse;
    d) stopping the further accumulation of said accumulatable quantity in response to said fourth pulse.

2. The method of claim 1 having the further improvement comprising the steps of:
    (a) arranging said experiment so that said accumulatable quantity is measure of the amount of time that has elapsed between the arrival of said first pulse and said third pulse at the experiment;
    (b) detecting a signal imposed on or created by said third pulse in said experiment initiated by said first pulse;
    (c) associating said signal with said accumulatable quantity for recording both values;
    (d) repeating steps (a) through (c) at differing time intervals between said pump pulse and said probe pulse to determine the temporal evolution of said event.

3. The method of claim 2, wherein said pump pulse is provided by a first source, and said probe pulse is provided by a second souce, and wherein said improvement further comprises the step of:
    (a) operating each said source so that at least one fourth pulses are detected at instants of time each of which falls between consecutive instants of time at which second pulses fall on said first detector means.

4. The method of claim 2 in which said pulses originate from different sources are arranged so that a representative number of time intervals between said first pulse and said third pulse is sampled in the time range of interest in the evolution of said event.

5. A method of performing pump/probe experiments, said method being of the type wherein a pump pulse and a probe pulse are directed at an experiment for initiating an event, and for probing said event for the purpose of observing the time-dependent behavior of said event, respectively, said method having the improvement comprising the steps of:
    a) splitting the pump pulse into a first and a second pulse, said first pulse being directed at said experiment for initiating said event therein, and said second pulse being directed at a detector means including a non-linear material;

b) splitting said probe pulse into third and fourth pulse, said third pulse being directed at said event for probing said event, and said fourth pulse also being directed at said detector means;

c) arranging said second and fourth pulses so that they overlap each other in said material for producing a measurable response at said detector means when they overlap, said measurable response on said detector being a measure of the time interval between the arrival of said first pulse and said third pulse at the experiment;

d) detecting an information signal imposed on (or created by) said third pulse by said event;

e) repeating steps (a) through (d) at differing time intervals between said pump pulse and said probe pulse, thereby obtaining step d) signals for observing the temporal evolution of said event.

6. The method of claim 5 in which said measurable response is produced by the overlap of said second pulse and said fourth pulse in said material whose nonlinearity produces a detectable quantity whose value is dependent on the time difference between said first pulse and said third pulse.

7. The method of claim 5 in which said measurable response at the detector is produced by the overlap of said second pulse and said fourth pulse in said material, said material producing a response which is at a wavelength that is different than the wavelength of the said second pulse and said fourth pulse.

8. The method of claim 5 in which said detector means responds to the variation in position of said overlap of said second pulse and said fourth pulse in said material, said position response being a measure of the time interval between the arrival of the pump pulse and probe pulse at the experiment.

9. The method of claim 5 in which said measurable response is produced by the overlap of said second pulse and said fourth pulse in said material whose nonlinearity produces a detectable quantity whose value is dependent on the time difference between said first pulse and said third pulse, and wherein said pump pulses and probe pulses originate from different sources operating independently of one another.

10. The method of claim 5, wherein said measurable response is produced by the overlap of said second pulse and said fourth pulse in said material whose nonlinearity produces a detectable quantity whose value is dependent on the time difference between said first pulse and said third pulse;
wherein said pump pulses and probe pulses originate from different sources operating independently of one another;
and wherein said measurable response for each pulse at the detector is produced by the overlap of said second pulse and said fourth pulse in said material, and said response is at a wavelength that is different from the wavelength of said second pulse and said fourth pulse.

11. The method of claim 5 wherein said measurable response is produced by the overlap of said second pulse and said fourth pulse in said material whose nonlinearity produces a detectable quantity whose value is dependent on the time difference between said first pulse and said third pulse;

wherein said pump pulses and probe pulses originate from different sources operating independently of one another;

and wherein said detector means responds to the variation in position of said overlap of said second pulse and said fourth pulse for each pulse, said position response being a measure of the time interval between the arrival of said first pulse and said third pulse at the experiment.

12. The invention of claim 11 in which said detector means, in response to the position of said overlap of said second pulse and said fourth pulse, controls the time interval between pump pulse and probe pulse, so that a representative number of time intervals between pump pulses and probe pulses are sampled in the time regime of interest.

13. A method of performing pump/probe experiments, said method being of the type wherein a pump pulse and a probe pulse are directed at an experiment for initiating an event, and for probing said event for the purpose of observing the time-dependent behavior of said event, respectively, the improvement comprising the steps of:

a) directing the pump pulse at said experiment for initiating a said event therein, and directing that portion of the pump pulse that is not absorbed onto a detector means including a nonlinear material, b) directing the probe pulse at said experiment for probing said event therein, and directing at least some of said probe pulse that has been altered by said experiment onto said detector means including said nonlinear material, c) arranging said non-absorbed portion of said pump pulse and said altered portion of said probe pulse so that a measurable response is produced at said detector means when they overlap, said measurable response on said detector being a measure of the time interval between the arrival of said first pump pulse and said probe pulse at the experiment;

d) repeating steps (a), (b) and (c) at differing time intervals between said pump pulse and said probe pulse to determine the temporal evolution of said event.

14. The method of claim 13 in which said measurable response is produced by the overlap of said second pulse and said fourth pulse at a place in said material whose nonlinearity produces a measurable quantity whose value is dependent on the time difference between said first pulse and said third pulse.

15. The method of claim 13 in which said measurable response at the detector is produced by the overlap of said second pulse and said fourth pulse at a place in said material, said material producing a response which is at a wavelength that is different than the wavelength of the said second pulse and said fourth pulse.

16. The method of claim 13 in which said detector means responds to the variation in position of the overlap of said second pulse and said fourth pulse at a place in said material, said position response being a measure of the time interval between the arrival of the pump pulse and probe pulse at the experiment.

17. The method of claim 13 in which said measurable response is produced by the overlap of said second pulse and said fourth pulse in said material whose nonlinearity produces a detectable quantity whose value is dependent on the time difference between said first pulse and said third pulse, and wherein said pump pulses and probe pulses originate from different sources operating independently of one another.

18. The method of claim 13, wherein said measurable response is produced by the overlap of said second pulse and said fourth pulse in said material whose nonlinearity produces a detectable quantity whose value is dependent on the time difference between said first pulse and said third pulse;
wherein said pump pulses and probe pulses originate from different sources operating independently of one another;
and wherein said measurable response for each pulse at the detector is produced by the overlap of said second pulse and said fourth pulse in said material, and said response is at a wavelength that is different from the wavelength of said second pulse and said fourth pulse.

19. The method of claim 13 wherein said measurable response is produced by the overlap of said second pulse and said fourth pulse in said material whose nonlinearity produces a detectable quantity whose value is dependent on the time difference between said first pulse and said third pulse;
wherein said pump pulses and probe pulses originate from different sources operating independently of one another;
and wherein said detector means responds to the variation in position of said overlap of said second pulse and said fourth pulse for each pulse, said position response being a measure of the time interval between the arrival of said first pulse and said third pulse at the experiment.

20. The invention of claim 13 in which said detector means, in response to the position of the overlap of said second pulse and said fourth pulse, controls the time interval between pump pulse and probe pulse, so that a representative number of time intervals between pump pulses and probe pulses are sampled in the time regime of interest.

21. In a system for observing time-dependent behavior of a pump pulse-initiated event in a pump/probe experiment, and wherein said system is of the type having means for producing pump pulses and probe pulses, pulse-directing means for directing one of said pump pulses at said experiment for initiating said event, and for directing one of said probe pulses at said event for having imposed thereon, or created thereby an information signal due to said event, signal detecting means for detecting said signal, and pulse detecting means, and said pulse-directing means also directing said pump pulse at said pulse detecting means and said probe pulse at said pulse detecting means, the improvement comprising
said pulse detecting means being responsive to said pump pulse and said probe pulse such as to produce a measure of the amount of time elapsed between the arrival at said experiment of the
said pump pulse and arrival at said experiment of the said probe pulse.

22. The invention of claim 21, wherein said improvement also comprises means responsive to said measure such as to produce an accumulatable quantity, and a data acquisition system for receiving both said quantity and said signal, and for storing same in association with each other.

23. The invention of claim 21, wherein as part of said improvement, detector means comprise first and second interdigitated photoconductors for producing photocurrent, at which said one pump pulse and said one probe pulse are respectively directed by said directing means, said photodetectors and accumulator means for receiving said current, said accumulator means being so constructed and arranged as to accumulate current of one of said photoconductors, but to cease accumulating same, in response to current from the other of said photoconductors.

24. A system for controlling the synchrony or asynchrony between two oscillator sources, said system comprising
a) detecting and responding to one of said oscillators by starting the accumulation of an accumulatable quantity in an accumulating means;
b) detecting and responding to said second of said oscillators by stopping the accumulation of said accumulatable quantity in said accumulating means;
said oscillators being so constructed and arranged that said accumulatable quantity is a measure of the synchrony or asynchrony of the two oscillators;
c) recording said accumulatable quantity;
d) repeating steps a) through d);
e) controlling the synchrony or asynchrony between the two oscillator sources by comparing said recorded values of said accumulatable quantity so as to provide an error signal that is used to modify the frequency of oscillation of the two sources.

25. A system for reducing the pulse timing jitter between two pulse sources consisting essentially of
a material in which the two pulses interact such that the change in the position of their overlap in the material is a measure of the time delay between the two pulses,
detector means constructed and arranged to be sensitive to the change in position of the two pulses that overlap in the material so as to produce a signal that can be used to bring the two pulse sources into synchrony.

26. The invention of claim 25 in which said material generates a pulse at a wavelength substantially different from the wavelength of each individual pulse.

27. The invention of claim 25 in which said detector is a CCD or diode array.

28. A system for programming the arrival time between pulses from two pulse sources consisting essentially of
a material in which the two pulses interact such that the change in the position of their overlap in the material is a measure of the time delay between the two pulses,
detector means constructed and arranged to be sensitive to the change in position of the two pulses that overlap in the material so as to produce a signal that can be used to program the time difference in arrival between two pulses at a point of interest.

29. The invention of claim 28 in which said material generates a pulse at a wavelength substantially different from the wavelength of each individual pulse.

30. The invention of claim 28 in which said detector is a CCD or diode array.

31. A time multiplier comprising a first source of a first quantity, a second source of a second quantity, and a third source of a third quantity, each said quantity being accumulatable;
said time multiplier also comprising a first accumulator means, a second accumulator means and a third accumulator means;

said first accumulator means being operatively connected to said first source, said second accumulator means being operatively connected to said second source, and said third accumulator means being operatively connected to said third source, each said accumulator means being constructed and arranged for accumulating quantity from the source to which it is connected;

said time multiplier means also comprising a comparator means operatively connected to said accumulator means for comparing the quantities accumulated by a pair of said accumulator means, and being responsive to the occurrence of a predetermined relationship between the quantities accumulated by said pair, such as to produce a control signal in response to said occurrence, and the remaining said accumulator means being connected to said comparator means for receiving said control signal and responding thereto by ceasing to accumulate said quantity;

each of said pair of accumulating means being constructed and arranged such as to accumulate quantities at a different rate of accumulation for causing said predetermined relationship to occur at the end of a time interval beginning with an original predetermined relationship.

32. The time multiplier of claim 31 wherein said first source is a power supply and said first quantity is electrically charge from said power supply, and said second source is a power supply and said second quantity is electrical charge from said power supply, and both said charges correspond to the same DC voltage;

said third source being a fast oscillator or clock and said third quantity being pulses or cycles produced by said fast oscillator or clock and said third accumulator means being a fast counter connected to said third source for counting up said pulses or cycles;

said first accumulator means being a first charging circuit, and said second accumulator means being a second charging circuit, one of said charging circuits having a time constant for charging, which is greater than the time constant for charging of the other of said charging circuit, and wherein the ratio between said time constants is chosen to be a desired time multiplication factor of said time multiplier;

said comparator means being connected to said charging circuits for producing said control signal when said charging circuits have charged to the same voltage;

and said fast counter being connected to said comparator means for receiving said control signal and, in response thereto, ceasing to count up said pulses or cycles;

and there being data acquisition means connected to said fast counter for receiving therefrom the number of pulses or cycles counted up by said fast counter by the time said comparator produces said control signal.

33. In a time-resolved spectroscopy system, wherein an event is initiated by pumping an experiment with pump pulses, and said event is probed by probe pulses; and wherein time-resolving means provides for measuring the time interval between a given pump pulse and a given probe pulse, the improvement wherein said time-resolving means comprises pump pulse detecting means, probe pulse detecting means, and accumulator means;

said pump pulse detecting means being constructed and arranged for receiving at least a portion of said given pump pulse, and in response producing a first accumulatable quantity;

said probe pulse detecting means being constructed and arranged for receiving at least a portion of said probe pulse, and in response producing as second accumulatable quantity; and said accumulator means being constructed and arranged for receiving said accumulatable quantities and providing a measure of the time-interval therebetween.

34. The invention of claim 33, wherein said accumulator means comprises charging means connected to both said detector means for being charged by said quantities;

said accumulator means also including accumulation control means responsive to said charging means.

35. The invention of claim 33, wherein said accumulator means comprises chargeable means connected to one said detector means for being charged in response to said one said detector means detecting a pulse, and to cease being charged when the other said detector means detects a pulse.

36. The invention of claim 35, wherein said chargeable means includes a capacitor, a DC power supply, and said one detector means being responsive to a pulse for connecting one side of said capacitor to one side of said power supply, and said other detector means being responsive to a pulse for short-circuiting said power supply; there being blocking means interconnecting said one detector means and said one side of said capacitor, and for allowing charge from said power supply to flow to said capacitor but preventing said charge from flowing in reverse.

37. The invention of claim 35 wherein said accumulator means comprises first and second chargeable means, and connector means, each said chargeable means being chargeable with said quantities to the same predetermined charge level, but at different rates whereby one said chargeable means reaches said charge level before the other;

said counter means being responsive to charging a said chargeable means for counting time during said charging; there being control means for detecting when both said chargeable means have reached said charge level and for thereupon stopping said counter means from counting time.

* * * * *